US012263375B2

(12) United States Patent
Dong et al.

(10) Patent No.: US 12,263,375 B2
(45) Date of Patent: Apr. 1, 2025

(54) EXTENSIBLE ELECTRODE ARRAY FOR ACCURATELY LOCATING A PELVIC FLOOR MUSCLE, DESIGN METHOD THEREOF AND EXTENSIBLE PELVIC FLOOR ELECTRODE

(71) Applicant: HaiNing Bernstein BioTech Co., Ltd., Jiaxing (CN)

(72) Inventors: Shurong Dong, Hangzhou (CN); Shengming Wang, Hangzhou (CN); Zhenwei Xie, Hangzhou (CN); Wei Guo, Hangzhou (CN)

(73) Assignee: GUANGZHOU HUIBO INFORMATION TECHNOLOGY CO., LTD., Guangzhou (CN)

(*) Notice: Subject to any disclaimer, the term of this patent is extended or adjusted under 35 U.S.C. 154(b) by 701 days.

(21) Appl. No.: 17/609,254

(22) PCT Filed: Dec. 4, 2020

(86) PCT No.: PCT/CN2020/134080
§ 371 (c)(1),
(2) Date: Nov. 5, 2021

(87) PCT Pub. No.: WO2022/068043
PCT Pub. Date: Apr. 7, 2022

(65) Prior Publication Data
US 2022/0314067 A1 Oct. 6, 2022

(30) Foreign Application Priority Data

Sep. 30, 2020 (CN) .......................... 202011063782.5
Sep. 30, 2020 (CN) .......................... 202022201598.4

(51) Int. Cl.
*A61B 5/22* (2006.01)
*A61B 5/00* (2006.01)
(Continued)

(52) U.S. Cl.
CPC .............. *A63B 23/20* (2013.01); *A61B 5/227* (2013.01); *A61B 5/4519* (2013.01); *A61N 1/0524* (2013.01)

(58) Field of Classification Search
CPC ........ A61B 5/227; A61B 5/4519; A63B 23/20
(Continued)

(56) References Cited

U.S. PATENT DOCUMENTS 7,822,482 B2   10/2010   Gerber
9,555,248 B2    1/2017   De Ridder

FOREIGN PATENT DOCUMENTS

CN       207679688       8/2018
CN       110123278       8/2019
(Continued)

*Primary Examiner* — Nadia A Mahmood
(74) *Attorney, Agent, or Firm* — Jiwen Chen; Joywin IP Law PLLC

(57) ABSTRACT

Disclosed is an extensible electrode array (102) for accurately locating a pelvic floor muscle, and its design method and an extensible pelvic floor electrode. The design method includes: (1) obtaining a three-dimensional muscle anatomy map of a pelvic floor muscle, dividing a muscle according to the three-dimensional muscle anatomy map and determining a muscle fiber trend, and for each muscle, determining a plurality of three-dimensional coordinate points for marking each muscle along the muscle fiber trend (S101); (2) after projecting all three-dimensional coordinate projects onto a two-dimensional plane unfolded in a shape of an elastic cavity (101), taking each two-dimensional coordinate point in the two-dimensional plane as a location to dispose an electrode plate (S102); (3) simulating a mechanical property of the elastic cavity (101), and determining a deformation rate of an extensible electrode wire (105) of the electrode plate when the extensible electrode wire (105) of the electrode plate is arranged along a muscle fiber direction of the pelvic floor muscle (S103); and (4) according to a design
(Continued)

result, mounting the electrode plate and the extensible electrode wire (105) on the elastic cavity (101) to form the extensible electrode array (102) (S104). The design method enables each electrode plate to locate the pelvic floor muscle before and after expansion, thereby improving accuracy in collecting a myoelectric signal of the pelvic floor muscle.

20 Claims, 4 Drawing Sheets

(51) Int. Cl.
 *A63B 23/20* (2006.01)
 *A61N 1/05* (2006.01)
(58) Field of Classification Search
 USPC .......................................................... 607/138
 See application file for complete search history.

(56) References Cited

FOREIGN PATENT DOCUMENTS

| | | |
|---|---|---|
| CN | 110464347 | 11/2019 |
| CN | 209645649 | 11/2019 |

EXTENSIBLE ELECTRODE ARRAY FOR ACCURATELY LOCATING A PELVIC FLOOR MUSCLE, DESIGN METHOD THEREOF AND EXTENSIBLE PELVIC FLOOR ELECTRODE

This is a U.S. national stage application of PCT Application No. PCT/CN2020/134080 under 35 U.S.C. 371, filed Dec. 4, 2020 in Chinese, claiming priority to Chinese Patent Applications No. 202022201598.4 filed Sep. 30, 2020, and Chinese Patent Applications No. 202011063782.5 filed Sep. 30, 2021, all of which are hereby incorporated by reference.

FIELD OF TECHNOLOGY

The present invention belongs to the field of biomedicine, and specifically relates to an extensible electrode array for accurately locating a pelvic floor muscle, a design method thereof and an extensible pelvic floor electrode.

BACKGROUND OF TECHNOLOGY

A myoelectric signal is one of the electrophysiological signals of a human body, as it is capable of reflecting physiological and pathological information of a body. Thus, it plays a vital role in clinical diagnosis, cognitive studies, driving robotic prosthetics and other fields. A high-density extensive electrode array is capable of providing a favorable biological fitness and signal restoring. In collecting surface myoelectricity, a differential electrode connection arranged along a muscle fiber direction is featured by high signal quality as compared with a single electrode connection, thus offering great help for subsequent signal analysis. Due to specialty of a collection location, in a high-density myoelectricity collection system, an electrode array needs to contact surface of a human body. Therefore, favorable biological fitness and signal anti-interference capability are required.

A pelvic floor muscle group of a woman has complicated compositions of muscles and a functional state of each muscle is inconsistent. Having a complicated anatomic structure is one of unique challenges for diseases and health care of a pelvic floor. A pelvic floor muscle electrophysiologial test method is one of the most scientific and accurate measures for diagnosing an abnormal functional state of a pelvic floor muscle. However, an electrode structure of the pelvic floor myoelectricity at present cannot accurately correspond to a functional state of a particular pelvic floor muscle.

In order to take functions of biological fitness and a high-density test of a human body's myoelectric signal into account, an inflating air bag electrode using a flexible electronic technique is an accurate measurement solution. For example, the invention patent application with a publication No. of CN110123278A discloses a stretchable high-density pelvic floor rehabilitation electrode. In a collection process, since physiological structures of each person are not totally the same, some inaccurate measurement results will appear: (1) due to different physiological conditions of each patient, it is very easy to generate an offset for a distribution location of an electrode of an air bag of an electrode array in a particular size, as a result of which it is easy to deviate from an original muscle measurement site in an expansion process of the air bag. Thus, a perfect adaptation to the general public cannot be achieved. (2) The existing concepts of selecting an electrode array and its differential pair are fuzzy and a differential pair electrode cannot ensure placement along a muscle fiber direction, resulting an error of a measurement signal. (3) Pelvic floor muscles are overlapped prevalently. In a focus region, it is easy to overlap a plurality of muscles. As a result, the existing electrode array cannot achieve reusing and analysis functions, resulting in failure of deep analysis on the signal. (4) Expansion of the air bag is easy to cause a change in a stress of an electrode surface, thus affecting stability of its electrical features and a measurement result. For the existing pelvic floor electrode, these problems are not considered comprehensively.

The existing high-density array pelvic floor electrode is generally divided into two types: one type refers to an electrode with a hard-cavity single-electrode connection, which is more convenient in manufacturing and collection. However, since its material is hard and it has less channels, accuracy of the signal and subsequent diagnosis are affected, resulting in failure of its application to an evaluation scene for accurate locating. The other type refers to a differential air bag electrode made of a high-density flexible material. As compared with the first type of the electrode, the electrode can ensure close contact of a sensing electrode with a human body, and ensure a signal to noise ratio of a collected surface myoelectric signal. However, the design of its electrode array is still simply close to the design of the electrode differential pair or the single electrode, without dividing a differential pair according to muscle fibers. Moreover, the effects of its deformation in the extending process on its features are not taken into account.

In addition, there are a number of electrode plates for an existing high-density pelvic floor rehabilitation electrode and these electrode plates are arranged at a regular array, but not to correspond to the pelvic floor muscle. Some electrode plates do not collect a pelvic floor muscle signal, resulting in chaos of subsequent myoelectric signals and waste of electrode plates. Moreover, the electrode plates employ a cascading circular shape formed by their arrangement in a form of a concentric circle. Moreover, upon air filling for the electrode plates in the cascading circular shape, a change occurs to impedance due to failure of releasing stress, resulting in instability of performances of the electrode.

Therefore, designing an electrode structure capable of accurately analyzing a trend of a featured pelvic floor muscle and ensuring stability of electrical features of the electrode under an expansion state has become a problem that urgently needs to be resolved.

SUMMARY OF THE INVENTION

In regard of the above, the first object of the present invention is to provide an extensible electrode array for accurately locating a pelvic floor muscle, and a design method thereof. According to decomposition of the pelvic floor muscle and an analysis result, the extensible electrode array and a manner of arranging its extensible electrode wire are designed to enable each electrode plate to locate the pelvic floor muscle before and after expansion, thus improving accuracy in collecting a myoelectric signal of the pelvic floor muscle.

The second object of the present invention is to provide an extensible pelvic floor electrode for accurately measuring electromyography of a pelvic floor muscle. An electrode plate of the extensible pelvic floor electrode can release the stress, enabling stability of properties of the entire electrode. Moreover, the number of electrode plates corresponds to that of pelvic floor muscles. Thus electrode plates required are fewer and of low cost.

In order to realize the first object of the present invention, the present invention provides a design method of an extensible electrode array for accurately locating a pelvic floor muscle, comprising the following steps:

(1) obtaining a three-dimensional muscle anatomy map of a pelvic floor muscle, dividing a muscle according to the three-dimensional muscle anatomy map and determining a muscle fiber trend, and for each muscle, determining a plurality of three-dimensional coordinate points for marking each muscle along the muscle fiber trend;

(2) after projecting all three-dimensional coordinate points onto a two-dimensional plane unfolded in a shape of an elastic cavity, taking each two-dimensional coordinate point in the two-dimensional plane as a location to dispose an electrode plate;

(3) simulating a mechanical property of the elastic cavity, and determining a deformation rate of an extensible electrode wire of the electrode plate when the extensible electrode wire of the electrode plate is arranged along a muscle fiber direction of the pelvic floor muscle; and (4) according to a designed location of the electrode plate, a wiring trend and the deformation rate of the extensible electrode wire, mounting the electrode plate and the extensible electrode wire on the elastic cavity to form the extensible electrode array for accurately locating a pelvic floor muscle.

Preferably, upon determining the plurality of three-dimensional coordinate points for marking each muscle along the muscle fiber trend, one three-dimensional coordinate point is at least determined at a center location of the muscle, and another one three-dimensional coordinate point is determined along the muscle fiber trend at 1-4 cm from the center location, wherein a differential electrode pair is composed by electrode plates disposed in correspondence to the two three-dimensional coordinate points.

Preferably, a distinguishing mark is disposed for each electrode plate and an extensible electrode wire thereof. For example, color distinguishing or numbering can be performed for each electrode plate and an extensible electrode wire connected thereon. The distinguishing mark forms a corresponding mapping relation of the electrode plate and the extensible electrode wire thereof to the pelvic floor muscle. According to the mapping relation, the pelvic floor muscle corresponding to each electrode plate can be obtained. In use, the myoelectric signal of each pelvic floor muscle can be accurately obtained according to the myoelectric signal collected by the electrode plate and the mapping relation.

Preferably, according to a simulation result for the mechanical property of the elastic cavity, an extensible electrode wire between two adjacent electrode plates is designed to be arranged in a sinusoidal shape or a U shape, and have a deformation rate of 0-50%. Arranging the extensible electrode wire in a sinusoidal shape or a U shape or other special shapes can provide sufficiently big extending space for the extensible electrode wire. In this way, when the extensible electric cavity expands, the extensible electrode wire can realize generation of 0-50% deformation rate with the expansion of the extensible elastic cavity.

Preferably, it is found from the simulation result for the mechanical property of the elastic cavity, upon expansion of the elastic cavity, the ratios of expansion from a deep portion to a shallow portion are not the same. The shallow portion closer to the handle has a smaller ratio of expansion. Similarly, upon expansion of the elastic cavity, the extensible electrode wire does not limit movement of the electrode array along with expansion of the elastic cavity. In the present invention, an extensible electrode wire between two adjacent electrode plates on each string is designed, and a minimum extending length of the extensible electrode wire between the electrode plates decreases sequentially along a direction from a deep portion to a shallow portion of the extensible pelvic floor electrode, wherein the minimum extending length is smaller than or equal to a maximum length of a pelvic floor muscle corresponding to the extensible electrode wire. Upon expansion of the elastic cavity, the corresponding relation of two electrode plates composing the differential electrode pair and the pelvic floor muscle is still invariable so as to accurately locate the pelvic floor muscle for collection of a pelvic floor muscle signal.

Due to individual differences, a size of a same pelvic floor muscle for each person also differs and a maximum length of the pelvic floor muscle is a length corresponding to a maximum pelvic floor muscle. Disposing the minimum value of the extensible length of the extensible electrode wire to be smaller than or equal to the maximum length of the pelvic floor muscle corresponding to the extensible electrode wire can ensure the electrode plate to be driven to move even if the elastic cavity expands to a maximum extent, and can also ensure correspondence of two adjacent electrode plates to one pelvic floor muscle for accurately collecting a myoelectric signal of the pelvic floor muscle.

Preferably, the electrode plate is designed as a flower shape, a radius of the electrode plate is 1 mm-20 mm and the number of petals is 2-20. In the electrode array, a deformable flower-shaped electrode is employed such that upon expansion of the elastic cavity, the stress generated on the electrode plate during internal air filling expansion can be released out along a circumferential direction through edges of the petals, thereby avoiding stress accumulated in some directions affecting integrity of the extensible pelvic floor electrode and stability of its impedance to electrical performance.

It is found from the simulation result for the mechanical property of the elastic cavity that since the expansion of the cavity is different axially and longitudinally, when the arrangement of electrodes and connecting relation of extensible electrode wires are invariable, the flower-shaped electrode should rotate at an angle that enables the direction of the majority of extensible electrode wires to be axial after being led out, thereby avoiding high stress in the longitudinal direction affecting electrical stability. Two ends of an extensible electrode wire between two adjacent electrode plates on each string are designed to be connected to petals of a flower-shaped electrode plate, and a direction of the extensible electrode wire is kept consistent with a direction where a stress of an air bag is small without affecting distribution and connection of the electrode plates.

Preferably, a structure of the extensible electrode array is designed to comprise a first insulating layer, a second insulating layer, a first conductive layer disposed on the second insulating layer, a second conductive layer disposed on another side of the second insulating layer, and a third insulating layer disposed on another side of the second conductive layer, wherein the first insulating layer, the second insulating layer and the third insulating layer are a non-extensible polymer material with a thickness of 1 μm-1 mm, the second insulating layer is provided with a through hole for guiding the extensible electrode wire, the first conductive layer and the second conductive layer are used for conducting an electrical signal, the first conductive layer comprises an electrode plate conductive portion and an extensible electrode wire conductive portion, the second conductive layer comprises an extensible electrode wire conductive portion, and a material of the first conductive layer and the second conducive layer is a metal or an alloy composed of two metals selected from copper, gold, silver, aluminum and titanium, with a thickness of 10 nm-2 mm.

Preferably, an electrode plate conductive portion of a first conductive layer of the extensible electrode array is designed with a coupling layer for coupling a myoelectric signal, and the coupling layer is one or a combination of at least two of a conductive gel, a silver chloride gel and a conductive carbon black.

In order to realize the first objective of the present invention, the present invention provides an extensible electrode array for accurately locating a pelvic floor muscle, wherein the extensible electrode array for accurately locating a pelvic floor muscle is designed and obtained through the design method of an extensible electrode array for accurately locating a pelvic floor muscle as described above.

In order to realize the second object of the present invention, the present invention provides an extensible pelvic floor electrode for accurately measuring electromyography of a pelvic floor muscle, comprising an extensible elastic cavity, an extensible electrode array, a handle and a pipe wherein the extensible electrode array is designed and obtained with the above design method, comprising an electrode plate and an extensible electrode wire, each electrode plate being of a flower shape; the extensible electrode array comprises N-2N electrode plates to form N differential electrode pairs, wherein N is a natural number greater than or equal to 3; two electrode plates of each differential electrode pair are disposed corresponding to one same pelvic floor muscle so as to detect an electromyography value of the pelvic floor muscle; the two electrode plates of the differential electrode pair and the extensible electrode wire connected thereon are provided with distinguishing marks, and are arranged and led out along a muscle fiber direction of a corresponding pelvic floor muscle; and the extensible electrode wire arranges the electrode plates into a string in a direction from a deep portion to a shallow portion, converges and leads them out to a location of the handle.

In the extensible electrode array, since the two electrode plates in the differential electrode pair correspond to one pelvic floor muscle and are arranged along a muscle fiber direction of the pelvic floor muscle, thus at most 2N electrode plates are employed to realize comprehensive collection of the myoelectric signal for measuring the pelvic floor muscle. Some muscles are connected to each other, in which case, the electrode plates can be reused for both collection of the myoelectric signal of one pelvic floor muscle and collection of the myoelectric signal of another pelvic floor muscle. Therefore, the extensible electrode array comprises N-2N electrode plates.

The deep portion to the shallow portion of the extensible pelvic floor muscle are relative concepts, as the position closer to the handle is the shallow portion of the extensible pelvic floor electrode and the position away from the handle is the deep portion of the extensible pelvic floor electrode. In the invention, the extensible electrode wire between electrode plates can be an extensible electrode wire which directly connects the electrode plates and is also for transmitting the myoelectric signal of a single electrode plate or can also be a converged extensible electrode wire which converges extensible electrode wires of a plurality of electrode plates together. The converging herein refers to converged arrangement, but it does not affect the myoelectric signal of each electrode plate. That is, myoelectric signals of electrode plates are independent of each other and the myoelectric signal of the electric plates is still transmitted independently through the extensible electrode wire connected thereto.

Preferably, for a differential electrode pair for measuring an electromyography value of a pelvic floor muscle, one electrode plate is located at a middle location of a muscle fiber, and the other electrode plate is arranged at 1-4 cm from the middle location along a muscle fiber direction.

In the extensible pelvic floor electrode, the extensible elastic cavity and the extensible electrode array are integrally molded, an electrode plate of the extensible electrode array is exposed on a surface of an extensible elastic cavity, and an extensible electrode wire of the electrode plate is embedded at the extensible elastic cavity.

In the extensible pelvic floor electrode, the extensible elastic cavity, the extensible electrode array and the extensible electrode wire are all extensible. After being filled with air or liquid through a pipe, the extensible elastic cavity expands. Upon expansion of the extensible elastic cavity, the extensible electrode wire does not limit movement of the extensible electrode array with expansion of the extensible elastic cavity. For each electrode plate, an extensible wire connected in correspondence thereto has two distributing manners: directing the extensible electrode wire conductive portion located at the first conductive layer onto the second conductive layer through the through hole of the first insulating layer for being led out, or directly leading out the extensible electrode wire conductive portion located at a first conductive layer; and when the number of extensible wire conductive portions converged on a same layer is greater than 1, employing a side-by-side manner for distribution and convergence such that myoelectric signals collected by each electrode plate do not affect each other.

Compared with the prior art, the advantageous effects of the present invention at least comprise:

in the design method provided by the present invention, according to decomposition of the pelvic floor muscle and an analysis result, the extensible electrode array and a manner of arranging its extensible electrode wire are designed to enable each electrode plate to locate the pelvic floor muscle before and after expansion, thus improving accuracy in collecting a myoelectric signal of the pelvic floor muscle.

In the designed extensible electrode array, the extensible electrode wire transmits the myoelectric signal independently, and converges them for arrangement and anticipates an extensible scope, thereby ensuring two adjacent electrode plates to still accurately locate the pelvic floor muscle when the expansion of the elastic cavity is suitable to pelvic floor muscles at different sizes, thereby accurately collecting the myoelectric signals.

In the designed extensible electrode array, each electrode plate and an extensible electrode wire connected thereto are provided with distinguishing marks, which can mark the pelvic floor muscle corresponding to each electrode plate. Moreover, the myoelectric signal of the pelvic floor muscle can be obtained accurately according to the myoelectric signal collected by the electrode plate and the distinguishing marks.

In the designed extensible electrode array, the flower-shaped electrode plate can release the stress generated by expansion of the elastic cavity through the edges of the petals, thereby avoiding stress accumulated affecting stability of the performance of the extensible pelvic floor electrode.

The extensible pelvic floor electrode provided by the present invention employs N-2N electrode plates and two adjacent electrode plates correspond to one pelvic floor muscle and are arranged along a muscle fiber direction of the pelvic floor muscle. In this way, each electrode plate is capable of collecting a myoelectric signal, such that waste of the electrode plates will not be caused while accurately locating the myoelectric signal of the pelvic floor muscle collected, resulting in requirement of less electrode plates, low cost and high locating efficiency.

BRIEF DESCRIPTION OF THE DRAWINGS

To describe the technical solutions in the embodiments of the present invention or in the prior art more clearly, the following briefly describes the accompanying drawings required for describing the embodiments or the prior art. Apparently, the accompanying drawings in the following description show merely some embodiments of the present invention, and a person of ordinary skill in the art may derive other drawings from these accompanying drawings without creative efforts.

DESCRIPTION OF THE EMBODIMENTS

To make the objects, technical solutions, and advantages of the present invention more comprehensible, the following describes the present invention in detail with reference to accompanying drawings and embodiments. It should be understood that the specific embodiments described herein are merely used to interpret the present invention, but not to limit the protection scope of the present invention.

Embodiment 1

Figure 1:
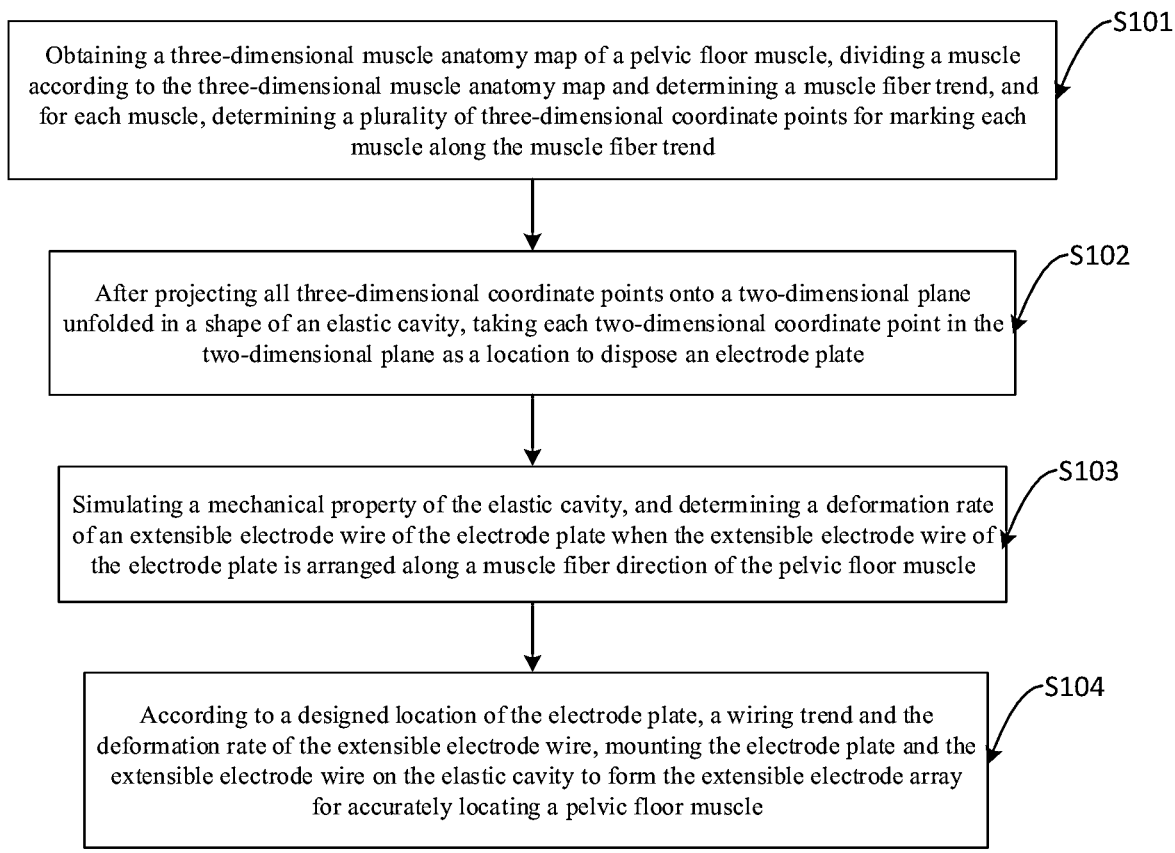
FIG. 1 is a flow chart of a design method of an extensible electrode array for accurately locating a pelvic floor muscle provided in embodiments.

FIG. 1 is a flow chart of a design method of an extensible electrode array for accurately locating a pelvic floor muscle provided in embodiment 1. As shown in FIG. 1, the design method comprises the following steps S101-S104.

S101: obtaining a three-dimensional muscle anatomy map of a pelvic floor muscle, dividing a muscle according to the three-dimensional muscle anatomy map and determining a muscle fiber trend, and for each muscle, determining a plurality of three-dimensional coordinate points for marking each muscle along the muscle fiber trend.

Figure 2:
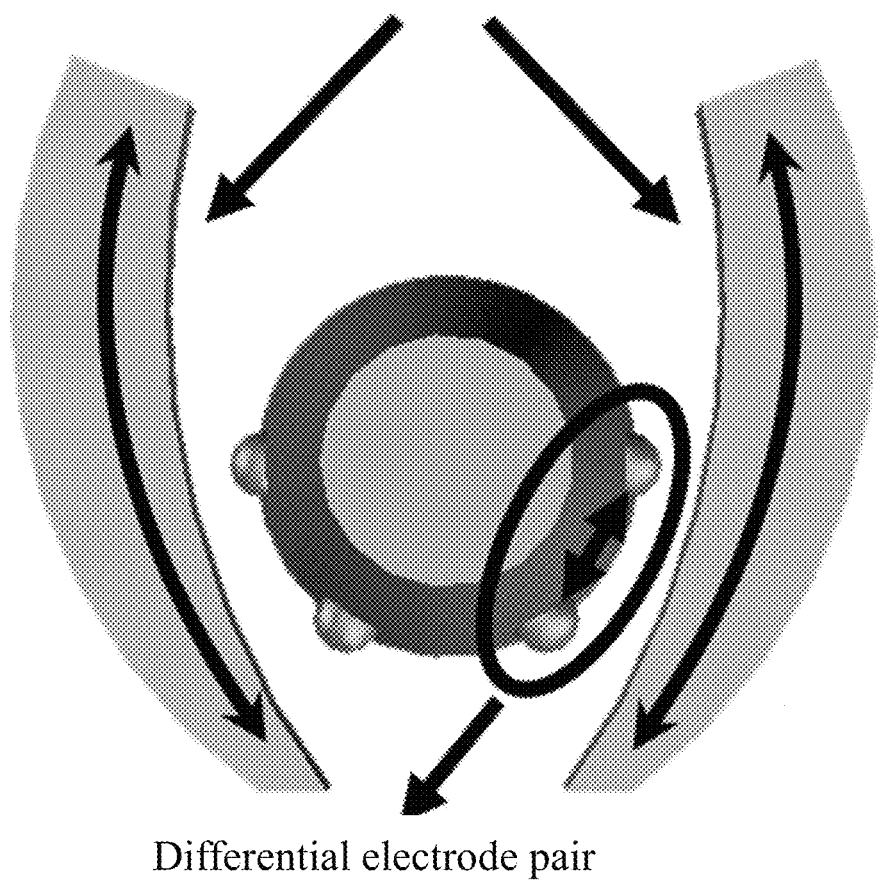
FIG. 2 is a diagram of a puborectal muscle provided in embodiments.

FIG. 2 shows a puborectal muscle in the three-dimensional muscle anatomy map and a muscle fiber trend as indicated by an arrow. In the embodiment, upon determining the plurality of three-dimensional coordinate points for marking each muscle along the muscle fiber trend, one three-dimensional coordinate point was at least determined at a center location of the muscle, and another one three-dimensional coordinate point was determined along the muscle fiber trend at 1-4 cm from the center location, wherein a differential electrode pair was composed by electrode plates disposed in correspondence to the two three-dimensional coordinate points.

S102: after projecting all three-dimensional coordinate projects onto a two-dimensional plane unfolded in a shape of an elastic cavity, taking each two-dimensional coordinate point in the two-dimensional plane as a location to dispose an electrode plate;

S103: simulating a mechanical property of the elastic cavity, and determining a deformation rate of an extensible electrode wire of the electrode plate when the extensible electrode wire of the electrode plate is arranged along a muscle fiber direction of the pelvic floor muscle.

In the embodiment, according to the simulation result for the mechanical property of the elastic cavity, an extensible electrode wire between two adjacent electrode plates was designed to be arranged in a sinusoidal shape or a U shape, and have a deformation rate of 0-50%.

Meanwhile, an extensible electrode wire between two adjacent electrode plates on each string was designed, and a minimum extending length of the extensible electrode wire between the electrode plates decreased sequentially along a direction from a deep portion to a shallow portion of the extensible pelvic floor electrode, wherein the minimum extending length was smaller than or equal to a maximum length of a pelvic floor muscle corresponding to the extensible electrode wire.

S104: according to a designed location of the electrode plate, a wiring trend and the deformation rate of the extensible electrode wire, mounting the electrode plate and the extensible electrode wire on the elastic cavity to form the extensible electrode array for accurately locating a pelvic floor muscle.

In the above design method, each electrode plate and its extensible electrode wire were further provided with distinguishing marks. Color distinguishing or numbering can be performed by the distinguishing marks for each electrode plate and an extensible electrode wire connected thereon. The distinguishing marks form a corresponding mapping relation of the electrode plate and the extensible electrode wire thereof to the pelvic floor muscle. According to the mapping relation, the pelvic floor muscle corresponding to each electrode plate can be obtained. In use, the myoelectric signal of each pelvic floor muscle can be accurately obtained according to the myoelectric signal collected by the electrode plate and the mapping relation.

In the above design method, each electrode plate was designed as a flower shape, a radius of the electrode plate was 2.5 mm as a maximum radius of a circle where a petal top was located, and the number of petals was 4. Meanwhile, two ends of an extensible electrode wire between two adjacent electrode plates on each string were designed to be connected to petals of a flower-shaped electrode plate, and a direction of the extensible electrode wire was kept consistent with a direction where a stress of an air bag was small without affecting distribution and connection of the electrode plates.

Figure 3:
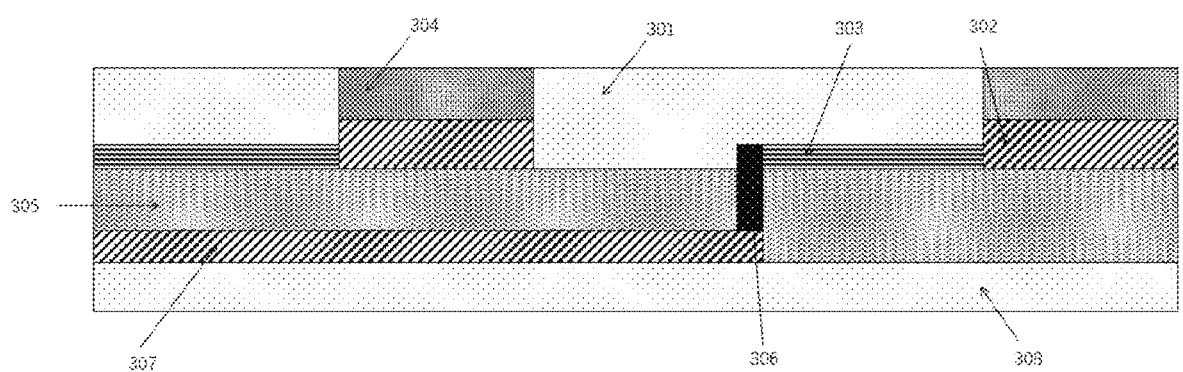
FIG. 3 is a structural diagram of an extensible electrode array provided in embodiments.

As shown in FIG. 3, the extensible electrode array comprises a first insulating layer 301, a first conductive layer electrode plate conductive portion 302, a first conductive layer extensible wire conductive portion 303, a coupling layer 304, a second insulating layer 305, a through hole 306, a second conductive layer 307 and a third insulating layer 308, wherein the first insulating layer 301 was used to isolate the first conductive layer extensible wire conductive portion 303 and its material was polyimide with a thickness of 0.2 mm, the first conductive layer electrode plate portion 302 and the first conductive layer extensible wire conductive portion 303 were disposed on one side of the second insulating layer 305 for conducting electricity, the material of the first conductive layer electrode plate portion 302 was gold-plated copper with a thickness of 0.4 mm, the material of the first conductive layer extensible wire conductive portion 303 was copper with a thickness of 0.256 mm, the material of the second insulating layer 305 was polyimide with a thickness of 0.2 mm, and the second insulating layer 305 was further provided with a through hole 306, through which the first conductive layer extensible wire conductive portion 303 can be connected to the second conductive layer 307 and then be converged and led out, and can also be directly converged and led out at the first conductive layer. When the number of extensible wire conductive portions converged at a same layer was greater than 1, a side-by-side manner was employed for distribution and converging. The material of the second conductive layer 307 was metal copper with a thickness of 0.135 mm. The extensible electrode wire between two adjacent electrode plates was arranged in a sinusoidal shape. The coupling layer 304 was disposed on the first conductive layer electrode plate conductive portion 302 for directly acting on skin to couple the myoeletric signal, and the material thereof was a conductive gel with a thickness of 0.2 mm. The third insulating layer 308 was disposed on another side of the second conductive layer 307 having a polyimide material with a thickness of 0.15 mm for isolating the second conductive layer. Employing such structure of the electrode plate can ensure no effect existing between extensible electrode wires connected to each electrode plate, thus enabling the myoelectric signals collected by each electrode plate not to affect each other. Reduction of a width of an entire wire by double-layer wiring can help to release stress upon deformation.

In the above design method, according to decomposition of the pelvic floor muscle and an analysis result, the extensible electrode array and a manner of arranging its extensible electrode wire were designed to enable each electrode plate to locate the pelvic floor muscle before and after expansion, thus improving accuracy in collecting a myoelectric signal of the pelvic floor muscle.

Embodiment 2

Figure 4:
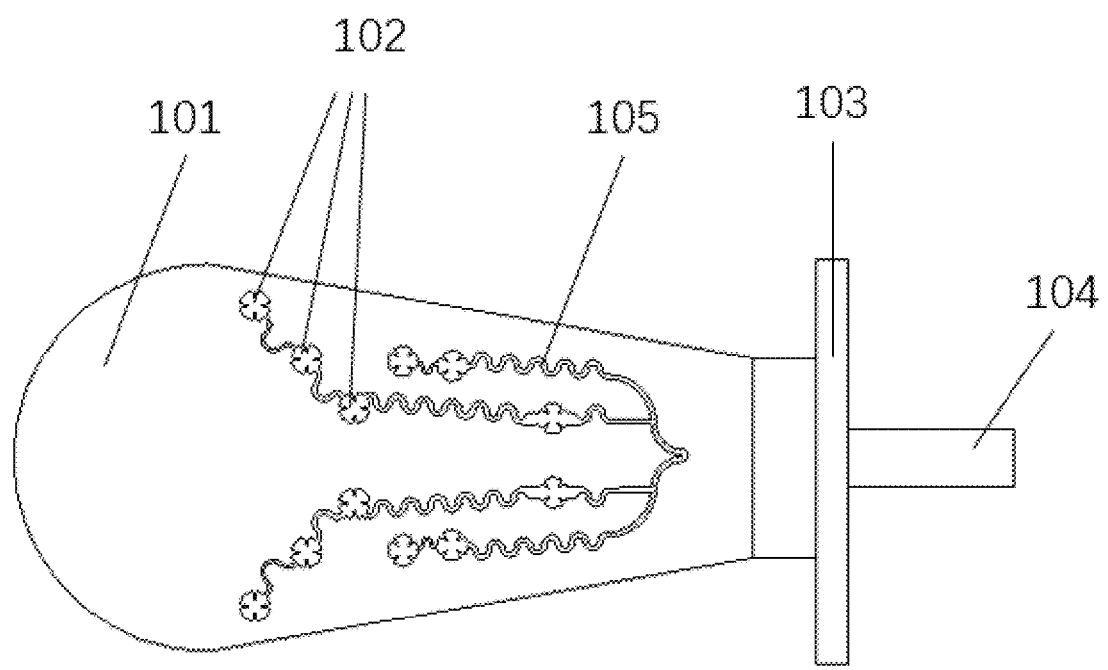
FIG. 4 is a structural diagram of an extensible pelvic floor electrode for accurately measuring electromyography of a pelvic floor muscle provided in embodiments.
Figure 5:
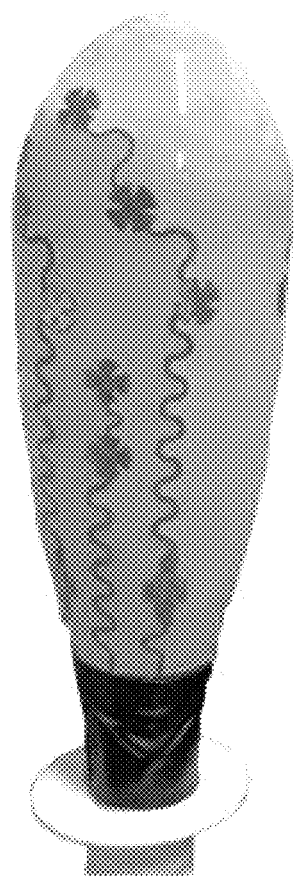
FIG. 5 is a physical map of an extensible pelvic floor electrode for accurately measuring electromyography of a pelvic floor muscle provided in embodiments.

FIG. 4 is a structural diagram of an extensible pelvic floor electrode for accurately measuring electromyography of a pelvic floor muscle provided in embodiments; FIG. 5 is a physical map of an extensible pelvic floor electrode for accurately measuring electromyography of a pelvic floor muscle provided in embodiments; and FIG. 3 is a structural diagram of an extensible electrode array provided in embodiments. As shown in FIG. 3 to FIG. 5, the embodiment provides an extensible pelvic floor electrode for accurately measuring electromyography of a pelvic floor muscle, comprising an elastic cavity 101, an extensible electrode array 102, a handle 103, a pipe 104 and an extensible electrode wire 105.

The extensible electrode array 102 comprises 36 electrode plates and each electrode plate was connected to one extensible electrode wire 105. 24 differential electrode pairs were composed with the 36 electrode plates. Two electrode plates of each differential electrode pair were disposed corresponding to one same pelvic floor muscle so as to detect an electromyography value of the pelvic floor muscle. The two electrode plates of the differential electrode pair and the extensible electrode wire connected thereon were provided with distinguishing marks, and were arranged and led out along a muscle fiber direction of a corresponding pelvic floor muscle, and the extensible electrode wire arranges the electrode plates into a string in a direction from a deep portion to a shallow portion, converges and leads them out to a location of the handle.

In embodiment 2, 6 pelvic floor muscles in total were measured and were arranged in a bilaterally symmetric structure. The number of differential pairs corresponding to each muscle differs according to a size of the muscle. Each electrode plate and an extensible electrode wire thereof were provided with distinguishing number, which forms a corresponding mapping relation of the electrode plate and the extensible electrode wire thereof to the pelvic floor muscle.

According to the mapping relation, the specific pelvic floor muscle corresponding to each electrode plate can be obtained. In use, the myoelectric signal of each pelvic floor muscle can be accurately obtained according to the myoelectric signal collected by the electrode plate and the mapping relation. In the extensible pelvic floor electrode, a minimum extending length of the extensible electrode wire between two adjacent electrode plates on each string decreases sequentially along a direction from a deep portion to a shallow portion of the extensible pelvic floor electrode, wherein the minimum extending length was smaller than or equal to a maximum length of a pelvic floor muscle corresponding to the extensible electrode wire. Two ends of an extensible electrode wire between two adjacent electrode plates on each string were directly connected to petals of a flower-shaped electrode plate, and a direction of the extensible electrode wire was kept consistent with a direction where a stress of an air bag was small without affecting distribution and connection of the electrode plates.

In embodiment 2, the electrode plate was in a deformable flower shape, a radius of the electrode plate was 2.5 mm as a maximum radius of a circle where a petal top was located, and the number of petals was 4. The specific extensible electrode array as shown in FIG. 3 was consistent with the descriptions in embodiment 1, such that it is not described again herein.

In the extensible pelvic floor electrode provided by the embodiment, the extensible elastic cavity and the extensible electrode array were integrally molded, an electrode plate of the extensible electrode array was exposed on a surface of an extensible elastic cavity, and an extensible electrode wire of the electrode plate was embedded at the extensible elastic cavity.

In the extensible pelvic floor electrode provided by the embodiment, each electrode plate and an extensible electrode wire thereof were provided with a wire number and a channel number for final evaluation was composed according to distribution, arrangement and combination of muscle fibers. One channel number represents one particular pelvic floor muscle. Since sizes of pelvic floor muscles were not the same, the number of channel numbers corresponding to each muscle was not the same either. For example, an electrode plate having a wire number 1 and an electrode plate having a wire number 2 that correspond to a vaginal sphincter muscle at a depth of 0 cm in a direction from 1 o'clock to 3 o'clock was recorded as channel number 1. An electrode having a wire number 2 and an electrode having a wire number 3 that correspond to vaginal sphincter muscle at a depth of 0 cm in a direction from 3 o'clock to 5 o'clock was recorded as channel number 2. Channel number 1 and channel number 2 reuse wire number 2 as one of a differential pair electrode. The detection targets of the pelvic floor electrode were 6 pelvic floor muscles, wherein vaginal sphincter muscle corresponds to 4 channel numbers, striated urethral sphincter corresponds to 4 channel numbers, external anal sphincter corresponds to 2 channel numbers, puborectal muscle corresponds to 4 channel numbers, pubococcygeus muscle corresponds to 4 channel numbers, and iliococcygeal muscle corresponds to 8 channel numbers.

The elastic cavity comprises an inner cavity formed by PDMS (polydimethylsiloxane) and an outer cavity formed by a rubber material, the inner cavity and the outer cavity being combined into a interlayer structure with a thickness of 1 mm for maintaining shape of the entire extensible pelvic floor electrode and bearing and supporting the electrode plate and the extensible electrode wire. The electrode plate was exposed on surface of the extensible elastic cavity and the extensible electrode wire was embedded in the interlayer structure of the extensible elastic cavity. A change in a contact area between a human body and an electrode imports interference of a myoelectric signal. The outer cavity was provided with an electrode hole. Due to presence a height differential between the outer cavity and the electrode plate, in order to improve stability of the signal and enhance signal restoring, the present invention enables to keep plane of the outer cavity flat by connecting a circular head of an extensible electrode and the outer cavity with hydrogel and can ensure sufficient contact of a conductive portion with a human body. Hydrogel was a polyvinyl alcohol material which was not toxic or harmful to a human body, such that it can be directly pasted to skin of a human body. The electrode plate was exposed on an outer surface of the cavity by passing through the electrode hole, and the extensible electrode wire of the electrode plate flows between the inner cavity and the outer cavity of the elastic cavity and was insulated from the outer surface. One end of the elastic cavity carries an input port, which was mounted with a pipe 104 for filling in gas or liquid, and the handle 103 was sleeved on the pipe of the input port. A gasket was further provided between the input port and the handle. The gasket mainly performs a function for support and fixing so as to prevent an electrode probe stretching excessively deep at introitus vaginae. The gasket can be of a disc-like shape having a circular hole at a center, and the circular hole of the center provides a channel for the pipe to facilitate the pipe to stretch into the cavity.

The pipe passes through the handle and the gasket and penetrates into the cavity through the input port. By filling the pipe with air or liquid, the elastic cavity will form a cylindrical or elliptical cavity having capability for expansion and contraction. The electrode array on the surface of the cavity was in close contact with an inner wall of the pelvic floor tract having complicated shapes. After air or liquid filling ends, a small hole on the pipe was closed to maintain full closure of the cavity and achieve a supporting effect through air pressure/water pressure. In use, the extensible pelvic floor electrode stretches into pelvis from vaginal when air was not filled for the extensible pelvic floor electrode. In this case, a doctor fills air or liquid into the inner cavity of the elastic cavity. By collecting electrode contract displayed on a collection page and inquiring subjective sense of a tester, the doctor determines an amount of air to be filled, directing the tester to perform Glazer pelvic floor muscle's evaluation and test.

In the foregoing specific implementations, technical solutions, and advantageous benefits of the present invention are described in detail. It should be understood that the foregoing descriptions are merely preferable embodiments of the present invention, but are not intended to limit the present invention. Any modification, supplement and equivalent replacement made within the principle of the present invention shall fall within the protection scope of the present invention.

What is claimed is:

1. A method of manufacturing an extensible electrode array for accurately locating a pelvic floor muscle, comprising the following steps:
   (1) obtaining a three-dimensional muscle anatomy map of a pelvic floor muscle, determining a target muscle group according to the three-dimensional muscle anatomy map and determining a muscle fiber trend, and for each muscle, determining a plurality of three-dimensional coordinate points for marking each muscle along the muscle fiber trend;
   (2) setting up an expandable elastic cavity with reference to shape of a pelvic floor cavity, after projecting all three-dimensional coordinate points onto a two-dimensional plane unfolded in a shape of an elastic cavity, taking each two-dimensional coordinate point in the two-dimensional plane as a location to dispose an electrode plate;
   (3) simulating a mechanical property of the elastic cavity under different expandable states, and determining a deformation rate of an extensible electrode wire of the electrode plate when the extensible electrode wire of the electrode plate is arranged along a muscle fiber direction of the pelvic floor muscle; and
   (4) according to a designed location of the electrode plate, a wiring trend and the deformation rate of the extensible electrode wire, mounting the electrode plate and the extensible electrode wire on the elastic cavity to form the extensible electrode array for accurately locating a pelvic floor muscle, and ensuring that each electrode plate maintains precise fit with the target muscle when the expandable elastic cavity expands.

2. The method as claimed in claim 1, wherein upon determining the plurality of three-dimensional coordinate points for marking each muscle along the muscle fiber trend, one three-dimensional coordinate point is at least determined at a center location of the muscle, and another one three-dimensional coordinate point is determined along the muscle fiber trend at 1-4 cm from the center location, wherein a differential electrode pair is composed by electrode plates disposed in correspondence to the two three-dimensional coordinate points.

3. The method as claimed in claim 1, wherein a distinguishing mark is disposed for corresponding muscle area of each electrode plate and an extensible electrode wire thereof.

4. The method as claimed in claim 1, wherein according to a simulation result for the mechanical property of the elastic cavity, an extensible electrode wire between two adjacent electrode plates is arranged in a sinusoidal shape or a U shape and have a deformation rate of 0-50% to fit with the expandable elastic cavity.

5. The method as claimed in claim 1, wherein according to a simulation result for the mechanical property of the elastic cavity, an extensible electrode wire between two adjacent electrode plates on each string is designed such that a minimum extending length of the extensible electrode wire between the electrode plates decreases sequentially along a direction from a deep portion to a shallow portion of an extensible pelvic floor electrode, wherein the minimum extending length is smaller than or equal to a maximum length of a pelvic floor muscle corresponding to the extensible electrode wire.

6. The method as claimed in claim 1, wherein the electrode plate is a flower shape, a radius of the electrode plate is 1 mm-20 mm and the number of petals is 2-20.

7. The method as claimed in claim 1, wherein according to a simulation result for the mechanical property of the elastic cavity, two ends of an extensible electrode wire between two adjacent electrode plates on each string are designed to be connected to petals of a flower-shaped electrode plate, and a direction of the extensible electrode wire is kept consistent with a direction where a stress of an air bag is small without affecting distribution and connection of the electrode plates, ensuring that when the elastic cavity expands, the extensible electrode wire can stretch freely with the elastic cavity and maintain conduction, maintaining the stability of signal transmission.

8. The method as claimed in claim 1, wherein a structure of the extensible electrode array comprises a first insulating layer, a second insulating layer, a first conductive layer disposed on the second insulating layer, a second conductive layer disposed on another side of the second insulating layer, and a third insulating layer disposed on another side of the second conductive layer, wherein the first insulating layer, the second insulating layer and the third insulating layer are a non-extensible polymer material with a thickness of 1 μm-1 mm, the second insulating layer is provided with a through hole for guiding the extensible electrode wire, the first conductive layer and the second conductive layer are used for conducting an electrical signal, the first conductive layer comprises an electrode plate conductive portion and an extensible electrode wire conductive portion, the second conductive layer comprises an extensible electrode wire conductive portion, and a material of the first conductive layer and the second conducive layer is a metal or an alloy composed of at least two metals selected from copper, gold, silver, aluminum and titanium, with a thickness of 10 nm-2 mm.

9. The method as claimed in claim 1, wherein an electrode plate conductive portion of a first conductive layer of the extensible electrode array is designed with a coupling layer for coupling a myoelectric signal, and the coupling layer is one or a combination of two of a conductive gel, a silver chloride gel and a conductive carbon black.

10. An extensible electrode array for accurately locating a pelvic floor muscle, wherein the extensible electrode array for accurately locating a pelvic floor muscle is made through the method as claimed in claim 1.

11. An extensible pelvic floor electrode for accurately measuring electromyography of a pelvic floor muscle, comprising:
an extensible elastic cavity,
an extensible electrode array,
a handle and a pipe,
wherein the extensible electrode array is made according to the method as claimed in claim 10, comprising an electrode plate and an extensible electrode wire, each electrode plate being of a flower shape; the extensible electrode array comprises N-2N electrode plates to form N differential electrode pairs, wherein N is a natural number greater than or equal to 3; two electrode plates of each differential electrode pair are disposed corresponding to one same pelvic floor muscle so as to detect an electromyography value of the pelvic floor muscle; the two electrode plates of the differential electrode pair and the extensible electrode wire connected thereon are provided with distinguishing marks, and are arranged and led out along a muscle fiber direction of a corresponding pelvic floor muscle; and the extensible electrode wire arranges the electrode plates into a string in a direction from a deep portion to a shallow portion, converges and leads them out to a location of the handle;
wherein extensible elastic cavity comprises an inner cavity formed by PDMS (polydimethylsiloxane) and an outer cavity formed by a rubber material; and the extensible elastic cavity is filled with air or liquid during use.

12. The extensible pelvic floor electrode for accurately measuring electromyography of a pelvic floor muscle as claimed in claim 11, wherein for a differential electrode pair for measuring an electromyography value of a pelvic floor muscle, one electrode plate is located at a middle location of a muscle fiber, and the other electrode plate is arranged at 1-4 cm from the middle location along the muscle fiber direction.

13. The extensible pelvic floor electrode for accurately measuring electromyography of a pelvic floor muscle as claimed in claim 11, wherein the extensible elastic cavity and the extensible electrode array are integrally molded, the electrode plate of the extensible electrode array is exposed on a surface of the extensible elastic cavity, and the extensible electrode wire of the electrode plate is embedded at the extensible elastic cavity.

14. The extensible pelvic floor electrode for accurately measuring electromyography of a pelvic floor muscle as claimed in claim 11, wherein for an extensible electrode wire between two adjacent electrode plates on each string, a minimum extending length of the extensible electrode wire between the electrode plates decreases sequentially along a direction from a deep portion to a shallow portion of the extensible pelvic floor electrode, wherein the minimum extending length is smaller than or equal to a maximum length of a pelvic floor muscle corresponding to the extensible electrode wire.

15. The extensible pelvic floor electrode for accurately measuring electromyography of a pelvic floor muscle as claimed in claim 11, wherein two ends of an extensible electrode wire between two adjacent electrode plates on each string are connected to petals of the flower-shaped electrode plate, and a direction of the extensible electrode wire is kept consistent with a direction where a stress of an air bag is small without affecting distribution and connection of the electrode plates.

16. The extensible pelvic floor electrode for accurately measuring electromyography of a pelvic floor muscle as claimed in claim 11, wherein a radius of each electrode plate is 1 mm-20 mm and the number of petals is 2-20.

17. The extensible pelvic floor electrode for accurately measuring electromyography of a pelvic floor muscle as claimed in claim 11, wherein the extensible electrode array comprises a first insulating layer, a second insulating layer, a first conductive layer disposed on the second insulating layer, a second conductive layer disposed on another side of the second insulating layer, and a third insulating layer disposed on another side of the second conductive layer, wherein the first insulating layer, the second insulating layer and the third insulating layer are a non-extensible polymer material with a thickness of 1 μm-1 mm, the second insulating layer is provided with a through hole for guiding the extensible electrode wire, the first conductive layer and the second conductive layer are used for conducting an electrical signal, the first conductive layer comprises an electrode plate conductive portion and an extensible electrode wire conductive portion, the second conductive layer comprises an extensible electrode wire conductive portion, and a material of the first conductive layer and the second conducive layer is a metal or an alloy composed of two metals selected from copper, gold, silver, aluminum and titanium, with a thickness of 10 nm-2 mm.

18. The extensible pelvic floor electrode for accurately measuring electromyography of a pelvic floor muscle as claimed in claim 17, wherein the extensible electrode array further comprises a coupling layer disposed on the electrode plate conductive portion of the first conductive layer and used for coupling a myoelectric signal, and the coupling layer is one or a mixing material of at least two of a conductive gel, a silver chloride gel and a conductive carbon black.

19. The extensible pelvic floor electrode for accurately measuring electromyography of a pelvic floor muscle as claimed in claim 16, wherein for each electrode plate, each extensible wire connected in correspondence thereto has two distributing manners: directing the extensible electrode wire conductive portion located at the first conductive layer onto the second conductive layer through the through hole of the first insulating layer for being led out, or directly leading out the extensible electrode wire conductive portion located at a first conductive layer; and when the number of extensible wire conductive portions converged on a same layer is greater than 1, employing a side-by-side manner for distribution and convergence such that myoelectric signals collected by each electrode plate do not affect each other.

20. The extensible pelvic floor electrode for accurately measuring electromyography of a pelvic floor muscle as claimed in claim 11, wherein an extensible electrode wire between two adjacent electrode plates is arranged in a sinusoidal shape or a U shape and has a deformation rate of 0-50%.

* * * * *